(12) United States Patent
Guennouni et al.

(10) Patent No.: US 7,884,225 B2
(45) Date of Patent: Feb. 8, 2011

(54) PROCESS FOR THE PREPARATION OF HALOGENOALKYLDIALKYL CHLOROSILANE

(75) Inventors: Nathalie Guennouni, Irigny (FR); Jean-Christophe Galland, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 0 days.

(21) Appl. No.: 12/173,968

(22) Filed: Jul. 16, 2008

(65) Prior Publication Data

US 2008/0275264 A1    Nov. 6, 2008

Related U.S. Application Data

(63) Continuation of application No. 10/561,223, filed as application No. PCT/FR2004/001487 on Jun. 16, 2004, now abandoned.

(30) Foreign Application Priority Data

Jun. 17, 2003    (FR) .................................. 03 50222

(51) Int. Cl.
*C07F 7/04* (2006.01)
(52) U.S. Cl. .................................................... 556/481
(58) Field of Classification Search ........................ None
See application file for complete search history.

(56) References Cited

U.S. PATENT DOCUMENTS

| | | | |
|---|---|---|---|
| 5,424,470 A | 6/1995 | Bank et al. | |
| 5,449,802 A | 9/1995 | Bank et al. | |
| 5,481,016 A | 1/1996 | Bank et al. | |
| 5,486,637 A | 1/1996 | Bank et al. | |
| 5,493,045 A | 2/1996 | Bank et al. | |
| 5,616,763 A | 4/1997 | Bank et al. | |
| 5,756,795 A | 5/1998 | Bank et al. | |
| 5,756,796 A | 5/1998 | Davern et al. | |
| 6,359,161 B2 * | 3/2002 | Tonomura et al. | 556/479 |
| 6,388,119 B1 * | 5/2002 | Bauer et al. | 556/479 |
| 6,500,977 B1 | 12/2002 | Dinh et al. | |
| 7,307,180 B2 | 12/2007 | Guennouni et al. | |
| 2001/0053861 A1 | 12/2001 | Tonomura et al. | |
| 2002/0052520 A1 | 5/2002 | Bauer et al. | |
| 2006/0167296 A1 | 7/2006 | Guennouni et al. | |

FOREIGN PATENT DOCUMENTS

| | | |
|---|---|---|
| DE | 10053037 C1 | 1/2002 |
| DE | 10232663 C1 | 10/2003 |
| EP | 0709390 B1 | 5/1996 |
| EP | 0722947 B1 | 7/1996 |
| EP | 0738730 B1 | 10/1996 |
| EP | 0738731 B1 | 10/1996 |
| EP | 0751140 A2 | 1/1997 |
| EP | 0786465 B1 | 7/1997 |
| EP | 0850943 A2 | 7/1998 |
| EP | 1156052 A2 | 11/2001 |
| JP | 07126271 A1 | 5/1995 |
| WO | WO 03/048169 * | 6/2003 |
| WO | WO 2004/009607 A1 | 1/2004 |

OTHER PUBLICATIONS

International Search Report corresponding to PCT/FR 2004/001487 issued on Dec. 15, 2004, 6 pages.
Nishibayashi et al., Organometallics (1995), 14(12), 5486-7.
Marinetti et al., Organometallics (1994), 13(10), 3956-62.

* cited by examiner

*Primary Examiner*—Daniel M Sullivan
*Assistant Examiner*—Chukwuma O Nwaonicha
(74) *Attorney, Agent, or Firm*—Buchanan Ingersoll & Rooney PC

(57) ABSTRACT

The present invention relates to a process for the preparation of 3-chloropropyldimethylchlorosilane by hydrosilylation reaction in a reaction medium comprising dimethylhydrochlorosilane and allyl chloride, in the presence of a catalytically effective amount of di-µ-chlorobis(η-1,5-cyclooctadiene)diiridium, the said process being characterized in that at least one auxiliary in the free or supported state selected from the group of compounds consisting of:
 (i) ketones,
 (ii) ethers,
 (iii) quinones,
 (iv) anhydrides,
 (v) unsaturated hydrocarbon compounds (UHC) having an aromatic nature and/or comprising at least one C═C double bond and/or at least one C≡C triple bond, it being possible for these unsaturated bonds to be conjugated or nonconjugated, the said UHCs being linear or cyclic (mono- or polycyclic), having from 4 to 30 carbon atoms, having from 1 to 8 ethylenic and/or acetylenic unsaturations and optionally comprising one or more heteroatoms,
 (vi) and their mixtures,
is added to the reaction medium, with the condition according to which, when the auxiliary comprises one or more UHCs as defined above, then this (these) UHC(s) is (are) mixed with at least one other auxiliary other than a UHC.

6 Claims, No Drawings

PROCESS FOR THE PREPARATION OF HALOGENOALKYLDIALKYL CHLOROSILANE

CROSS-REFERENCE TO PRIORITY/PROVISIONAL APPLICATIONS

This application is a continuation of application Ser. No. 10/561,223, filed Feb. 27, 2007 now abandoned, which claims priority under 35 U.S.C. §119 of FR 03/50222, filed Jun. 17, 2003, and is the National Phase of PCT/FR 2004/001487, filed Jun. 16, 2004 and designating the United States, published on Dec. 29, 2004 as WO 2004/113354 A2, each hereby expressly incorporated by reference and each assigned to the assignee hereof.

The present invention relates to a process for the preparation of haloalkyldialkylhalosilane.

More particularly, the present invention relates to a process for the preparation of 3-halopropyldimethylchlorosilane by hydrosilylation of dimethylhydrochlorosilane using allyl chloride and a catalyst based on a platinum ore metal, in particular iridium, and optional recovery of the said metal. The reaction involved in this example is as follows:

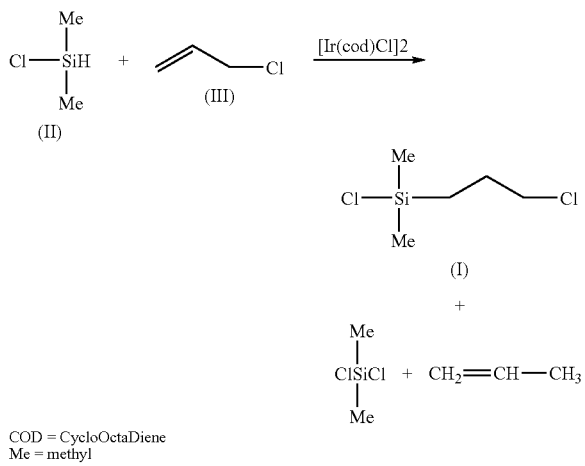

COD = CycloOctaDiene
Me = methyl

In this type of reaction, the amounts of platinum ore metal involved are often high with the aim of obtaining a satisfactory yield. Under these conditions, in order for the process to remain economically advantageous, it is necessary to recover the platinum ore metal in order to be able to reuse it as catalyst.

Another route for improving the economics of the process would be to optimize the activity of the catalyst. To do this, it is arranged for the degree of conversion (DC) of the hydrosilane (II) to be increased or, for a given DC, for the selectivity (S) of the catalyst to be significantly increased.

In the present account, the degree of conversion (DC) and the selectivity (S) correspond to the following definitions:

$$TT = \frac{\text{number of moles of SiH units consumed}}{\text{number of moles of SiH units or of } (II) \text{ introduced}}$$

$$S = \frac{\text{number of moles of } (I)}{\text{number of moles of SiH units or of } (II) \text{ introduced}}$$

The hydrosilylation of allyl chloride by dimethylhydrochlorosilane catalyzed by an iridium-based catalyst is disclosed in the following patent documents: JP-B-2938731 and JP-A-7126271. The catalysts disclosed in these patent documents are of the [Ir(diene)Cl]$_2$ type and make possible access to full degrees of conversion (DC=100%) of the dimethylhydrochlorosilane with a good selectivity of the reaction (good yield YD of 3-chloropropyldimethylchlorosilane). However, these performances are achieved at the cost of very large amounts of catalyst.

EP-A-1 156 052 (=U.S. Pat. No. 6,359,161) and DE-A-10053037 (US-A-2002/0052520) disclose:

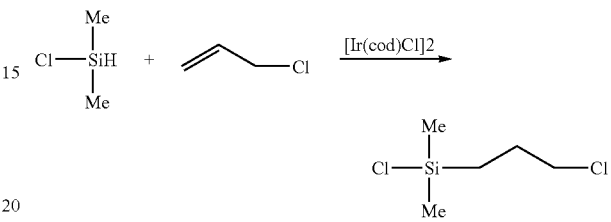

in the presence of free COD for increasing the yield:
EP-A-1 156 052: $4\times10^{-3}$ mol of free COD per $1\times10^{-4}$ mol of [Ir(COD)Cl]$_2$: i.e. a ratio of 40,
versus DE-A-10053037: $9.2\times10^{-4}$ mol of free COD per $4.5\times10^{-6}$ mol of [Ir(COD)Cl]$_2$: i.e. a ratio of 204.

BE-B-785343 (U.S. Pat. No. 3,798,252) discloses the hydrosilylation of allyl chloride by trichlorohydrosilane in the presence of chloroplatinic acid in solution in cyclohexanone (removal of water from the solution using Na$_2$SO$_4$). The ketone is combined with the platinum in order to improve the selectivity of the reaction.

In this state of the art, one of the essential objects of the present invention is to provide a means which makes it possible to optimise the activity of the iridium-based catalyst in comparison with what is taught in the prior art [in particular EP-A-1 156 052 (=U.S. Pat. No. 6,359,161) and DE-A-10053037 [US-A-2002/0052520].

Another essential object of the invention is to provide a process for the preparation of a haloalkyldialkylhalosilane of the above type which is effective, economical and easy to implement.

These objects, among others, are achieved by the invention, which relates, first, to a process for the preparation of a haloalkyldialkylhalosilane of formula (I):

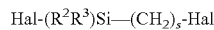

by hydrosilylation reaction of a reaction medium comprising:
a silane of formula (II):

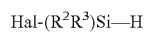

and an alkenyl halide of formula (III):

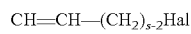

in the presence of a catalytically effective amount of a hydrosilylation catalyst based on iridium in the oxidation state I or III, in which formulae (I), (II), (III):
the symbol Hal represents a halogen atom chosen from the chlorine, bromine and iodine atoms,
the symbols $R^2$ et $R^3$, which are identical or different, each represent a monovalent hydrocarbon group chosen from a linear or branched alkyl radical having from 1 to 6 carbon atoms and a phenyl radical, and
s represents an integer between 2 and 10 inclusive, the said process being characterized in that at least one auxiliary in the free or supported state selected from the group of compounds consisting of:
(i) ketones,
(ii) ethers,
(iii) quinones,
(iv) anhydrides,
(v) unsaturated hydrocarbon compounds (UHC) having an aromatic nature and/or comprising at least one C=C double bond and/or at least one C≡C triple bond, it being possible for these unsaturated bonds to be conjugated or nonconjugated, the said UHCs being linear or cyclic (mono- or polycyclic), having from 4 to 30 carbon atoms, having from 1 to 8 ethylenic and/or acetylenic unsaturations and optionally comprising one or more heteroatoms,
(vi) and their mixtures, is added to the reaction medium, with the condition according to which, when the auxiliary comprises one or more UHCs as defined above, then this (these) UHC(s) is (are) mixed with at least one other auxiliary other than a UHC.

In accordance with the present invention, the term "mixtures (vi)" of auxiliary compounds is understood in particular to mean:
(vi.1) any mixture of compounds (I) and/or (ii) and/or (iii) and/or (iv) and/or (v),
(vi.2) any compound having a molecule comprising at least two different chemical functional groups selected from the group consisting of the ketone, ether, anhydride, quinone, C=C and C≡C functional groups characteristic of the compounds (i) to (v),
(vi.3) any mixture of compounds (vi.2),
(vi.4) and any mixture based on at least one compound (i) to (v) and on at least one compound (vi.2).

According to a preferred form, use is made of a catalyst based on iridium in the oxidation state I, in the structure of which each iridium atom corresponds to the complex form of the $Ir(L)_3X$ type where the symbols L and X have the definitions given in the work "Chimie Organométallique" [Organométallic Chemistry] by Didier Astruc, published in 2000 by EDP Sciences (cf. in particular page 31 et seq.).

According to a more preferred form, the catalyst corresponds to the formula (IV):

$$[Ir(R^4)_x(R^5)]_y \quad (IV)$$

in which:
the symbol $R^4$ represents either a monodentate ligand L, and in this case x=2, or a bidentate ligand $(L)_2$, and in this case x=1, and
the symbol $R^5$ represents either Hal as defined above, and in this case y=2, or a ligand of type LX, and in this case y=1.

Catalysts corresponding to the more preferred definition mentioned above in which:
$R^4$ is a ligand comprising at least one C=C double bond and/or at least one C≡C triple bond, it being possible for these unsaturated bonds to be conjugated or nonconjugated, the said ligand being linear or cyclic (mono- or polycyclic), having from 4 to 30 carbon atoms, having from 1 to 8 ethylenic and/or acetylenic unsaturations and optionally comprising one or more heteroatoms, and
$R^5$, in addition to Hal, can also represent a ligand LX, such as in particular a ligand derived from acetylacetone, from a β-ketoester, from a malonic ester or from an allyl compound,
are highly suitable.

According to an even more preferred form, the catalyst corresponds to the formula (IV) where the symbol $R^5$ of the catalyst represents Hal and y=2.

The ligands $R^4$ of the preferred catalyst (IV) can be identical to or different from the UHCs (v) of the auxiliary.

The iridium-based catalyst can be supported, as is disclosed, for example, in U.S. Pat. No. 6,177,585 and GB-A-1 526 324.

The catalytic system used in accordance with the process according to the invention makes it possible to reduce the amount of catalyst necessary for the achievement of a full degree of conversion DC of the silane of formula (II): (Hal-$(R^2R^3)Si$—H) and/or to increase the selectivity S for a given and fixed DC.

This catalytic system is advantageously composed:
of an organometallic catalyst based on iridium in the oxidation state I or III,
of one or more auxiliaries each introduced in a minimum amount of 20 mol % with respect to the metal.

This or these auxiliaries can be used in the liquid or solid form. Provided that they are liquid, they can be introduced in an amount such that, in the reaction medium, they, in addition to acting as hydrosilylation promoter, act as solvent for the reaction.

The fact of being able to be employed in liquid form is a very major operational advantage for the process of the invention.

The possible function of solvent of the auxiliary can also make it possible, in particular when it is a heavy solvent (namely, a solvent having a boiling point at atmospheric pressure which is greater than that of the compound of formula (I), such as, for example, a polyether), to improve the stability of the reaction medium and thus the safety of the process. In addition, this offers possibilities of easy recovery of the catalyst and thus of recycling the latter.

When the auxiliary is in the free state, it can be introduced into the reaction medium according to a molar ratio, with respect to the iridium metal, of at least 0.2, preferably of at least 1. Depending on the nature of the ligands, a molar ratio of greater than 10 and even of greater than 100 can more preferably be chosen.

In the case where the auxiliary comprises at least one compound selected from the group of the UHCs (v), taken by themselves or as mixtures with one another, the concentration of catalyst (preferably IV) is such that the iridium/silane of formula (II) molar ratio is less than or equal to $400 \times 10^{-6}$, preferably less than or equal to $200 \times 10^{-6}$ and more preferably still less than or equal to $50 \times 10^{-6}$.

Reference may be made, as examples of suitable ketones (i), to those defined in U.S. Pat. No. 3,798,252 et in PL-A-176036, PL-A-174810, PL-A-145670 and JP-A-75024947.

Reference may be made, as examples of suitable ethers (ii), to those defined in U.S. Pat. No. 4,820,674 and in JP-A-52093718.

Advantageously, the auxiliary is selected from the group consisting in particular of: cyclohexanone, 2-cyclohexen-1-one, isophorone, 2-benzylidenecyclohexanone, 3-methylene-2-norbornanone, 4-hexen-3-one, 2-allylcyclohexanone, 2-oxo-1-cyclohexanepropionitrile, 2-(1-cyclohexenyl)cyclohexanone, monoglyme, ethylene glycol divinyl ether, ethyl ether, benzoquinone, phenylbenzoquinone, maleic anhydride, allyl succinic anhydride, 3-benzylidene-2,4-pentadione, phenothiazine, (methylvinyl)cyclotetrasiloxane (vinylated D4), 4-phenyl-3-butyn-2-one, 1,3-butadiene, 1,5-hexadiene, 1,3-cyclohexadiene, 1,5-cyclooctadiene (COD), 1,5,9-cyclododecatriene, divinyltetramethylsiloxane (DVTMS), norbornadiene and their mixtures.

According to a preferred embodiment of the invention, the auxiliary (vi) comprising at least one UHC (v), preferably COD, and at least one ketone (i), preferably cyclohexanone, and/or at least one ether (ii) and/or at least one quinone (iii).

In this preferred embodiment of the process according to the invention, the concentration of catalyst, preferably of formula (IV), is such that the iridium/silane of formula (II) molar ratio is less than or equal to $100 \times 10^{-6}$, preferably less than or equal to $60 \times 10^{-6}$, and more preferably still is between $40 \times 10^{-6}$ and $1 \times 10^{-6}$.

According to a procedure specific to this preferred embodiment, the components of the mixture (vi), UHC/(i) and/or (ii) and/or (iii), are present in the reaction medium when the reaction begins.

Mention will be made, as examples of iridium complexes of formula (IV) which are especially well suited, of those corresponding to the even more preferred form, in the formula of which the symbol $R^4$ is a ligand chosen from 1,3-butadiene, 1,5-hexadiene, 1,3-cyclohexadiene, 1,5-cyclooctadiene (COD), 1,5,9-cyclododecatriene, divinyltetramethylsiloxane and norbornadiene.

Mention will be made, as specific examples of iridium complexes (IV) which are even better suited, of the following catalysts:

di-μ-chlorobis(η-1,5-hexadiene)diiridium,
di-μ-bromobis(η-1,5-hexadiene)diiridium,
di-μ-iodobis(η-1,5-hexadiene)diiridium,
di-μ-chlorobis(η-1,5-cyclooctadiene)diiridium,
di-μ-bromobis(η-1,5-cyclooctadiene)diiridium,
di-μ-iodobis(η-1,5-cyclooctadiene)diiridium,
di-μ-chlorobis(η-2,5-norbornadiene)diiridium,
di-μ-bromobis(η-2,5-norbornadiene)diiridium,
di-μ-iodobis(η-2,5-norbornadiene)diiridium.

The process according to the invention can be employed either continuously, semicontinuously or batchwise.

These three operating methods are suitable in particular when the catalyst, preferably IV, is used in a homogeneous liquid medium, according to a preferred arrangement of the invention and as disclosed in JP-B-2 938 731 and EP-A-1 156 052.

Preferably, the product of formula (I) is 3-chloropropyldimethylchlorosilane, the product of formula (II) is dimethylhydrochlorosilane and the product of formula (III) is allyl chloride.

According to another of its aspects, the invention relates to a catalytic system for the preparation of a haloalkyldialkylhalosilane of formula (I):

$$\text{Hal-}(R^2R^3)\text{Si—}(CH_2)_s\text{-Hal}$$

by hydrosilylation reaction of a reaction medium comprising:
a silane of formula (II):

$$\text{Hal-}(R^2R^3)\text{Si—H}$$

and an alkenyl halide of formula (III):

$$CH_2\!\!=\!\!CH\text{—}(CH_2)_{s-2}\text{Hal}$$

in which formulae:
the symbol Hal represents a halogen atom chosen from the chlorine, bromine and iodine atoms,
the symbols $R^2$ et $R^3$, which are identical or different, each represent a monovalent hydrocarbon group chosen from a linear or branched alkyl radical having from 1 to 6 carbon atoms and a phenyl radical, and s represents an integer between 2 and 10 inclusive, characterized in that it comprises:
1—a hydrosilylation catalyst based on iridium in the oxidation state I, in the structure of which each iridium atom corresponds to the complex form of the Ir(L)$_3$X type where the symbols L and X have the definitions given in the work "Chimie Organométallique" [Organometallic Chemistry] by Didier Astruc, published in 2000 by EDP Sciences (cf. in particular page 31 et seq.), this catalyst preferably corresponding to the formula:

$$[\text{Ir}(R^4)_x(R^5)]_y \qquad (IV)$$

in which:
the symbol $R^4$ represents either a monodentate ligand L, and in this case x=2, or a bidentate ligand (L)$_2$, and in this case x=1, and
the symbol $R^5$ represents either Hal, Hal representing a halogen atom chosen from chlorine, bromine and iodine atoms, and in this case y=2, or a ligand of type LX, and in this case y=1,
2—and at least one auxiliary in the free or supported state selected from the group of compounds consisting of:
(i) ketones,
(ii) ethers,
(iii) quinones,
(iv) anhydrides,
(v) unsaturated hydrocarbon compounds (UHC) having an aromatic nature and/or comprising at least one C=C double bond and/or at least one C≡C triple bond, it being possible for these unsaturated bonds to be conjugated or nonconjugated, the said UHCs being linear or cyclic (mono- or polycyclic), having from 4 to 30 carbon atoms, having from 1 to 8 ethylenic and/or acetylenic unsaturations and optionally comprising one or more heteroatoms,
(vi) and their mixtures, with the condition according to which, when the auxiliary comprises one or more UHCs as defined above, then this (these) UHC(s) is (are) mixed with at least one other auxiliary other than a UHC.

EXAMPLES

The following examples illustrate the invention without limiting the scope thereof. They have the object of evaluating catalytic systems: [di-μ-chlorobis(η-1,5-cyclooctadiene)diiridium+hydrosilylation auxiliary(ies)] in the reaction for the hydrosilylation of allyl chloride by dimethylhydrochlorosilane.

The tests are carried out in parallel reactors.

Each reactor is equipped with a magnetic stirrer, with a reflux condenser and with a thermometer. The heat-exchange fluid is brought to a temperature of −35° C., which makes it possible to obtain a material balance always greater than 95% by weight.

The effect of the hydrosilylation auxiliaries is compared with a control reaction, where only di-μ-chlorobis(η-1,5-cyclooctadiene)diiridium was used. For this control test, an intentionally low amount of catalyst was introduced in order to obtain a degree of conversion of the corresponding SiH functional groups of the order of 50%.

The dimethylhydrochlorosilane, with a purity of 99% by weight, is added by running onto a heel, composed of the allyl chloride (1.05 mol. eq./silane) and of the catalytic system

[di-μ-chlorobis(η-1,5-cyclooctadiene)diiridium+hydrosilylation auxiliary(ies)] heated to 35° C. The silane is run in via a syringe driver at a flow rate of 1.3 ml/minute. The temperature of the reaction medium is not regulated.

The reaction medium is analyzed by gas chromatography calibrated with n-tetradecane.

I: Hydrosilylation Auxiliaries Used Alone:

1.1—Effect of the Ketones (i):

TABLE I

| Example | Ketone | Ketone/Ir molar ratio | Ir/ClMe$_2$SiH molar ratio ($\times 10^{-6}$) | DC (%) | S (%) |
|---|---|---|---|---|---|
| 1 | None | 0 | 235 | 94 | 76 |
| 2 | Cyclohexanone | 100 | 235 | 80 | 91 |
| 3 | None | 0 | 130 | 50 | 82 |
| 4 | 2-Cyclohexen-1-one | 91 | 133 | 44 | 91 |
| 5 | 2-Allylcyclohexanone | 100 | 133 | 41 | 92 |
| 6 | 2-(1-Cyclohexenyl)-cyclohexanone | 137 | 132 | 51 | 90 |
| 7 | 3-Benzylidene-2,4-pentadione | 1.2 | 131 | 59 | 81 |
| 8 | 3-Benzylidene-2,4-pentadione | 115 | 134 | 42 | 92 |

1.2—Effect of the Ethers (ii):

TABLE II

| Example | Ether | Ether/Ir molar ratio | Ir/ClMe$_2$SiH molar ratio ($\times 10^{-6}$) | DC (%) | S (%) |
|---|---|---|---|---|---|
| 3 | None | 0 | 130 | 50 | 82 |
| 9 | Monoglyme | 109 | 131 | 60 | 81 |
| 10 | Monoglyme | 260 | 136 | 45 | 86 |
| 11 | Ethyl ether | 740 | 134 | 60 | 89 |

1.3—Effect of the Quinones (iii):

TABLE III

| Example | Quinone | Quinone/Ir molar ratio | Ir/ClMe$_2$SiH molar ratio ($\times 10^{-6}$) | DC (%) | S (%) |
|---|---|---|---|---|---|
| 3 | None | 0 | 130 | 50 | 82 |
| 12 | Benzoquinone | 93 | 141 | 40 | 94 |
| 13 | Phenylbenzoquinone | 1.1 | 137 | 51 | 84 |

1.4—Effect of the Anhydrides (iv):

TABLE IV

| Example | Anhydride | Anhydride/Ir molar ratio | Ir/ClMe$_2$SiH molar ratio ($\times 10^{-6}$) | DC (%) | S (%) |
|---|---|---|---|---|---|
| 3 | None | 0 | 130 | 50 | 82 |
| 14 | Allyl succinic anhydride | 103 | 133 | 47 | 87 |
| 15 | Maleic anhydride | 1.7 | 131 | 43 | 84 |

1.5—Effect of the UHC Auxiliaries (v):

TABLE V

| Example | UHC (v) | R$^4$/Ir molar ratio | Ir/ClMe$_2$SiH molar ratio ($\times 10^{-6}$) | DC (%) | S (%) |
|---|---|---|---|---|---|
| 3 | None | 0 | 130 | 50 | 82 |
| 16 | Vinylated D4 | 104 | 135 | 48 | 86 |
| 17 | Phenothiazine | 1.1 | 132 | 55 | 83 |

II: Combination of Hydrosilylation Auxiliaries

II. 1—Combination of Cyclohexanone and of 1,5-Cyclooctadiene (1,5-COD):

TABLE VI

| Example | Ir/ClMe$_2$SiH ($\times 10^{-6}$) | DC (%) | S (%) | Cyclohexanone/Ir molar ratio | 1,5-COD/Ir molar ratio |
|---|---|---|---|---|---|
| 18 | 51 | 21 | 70 | — | — |
| 19 | 49 | 15 | 82 | 189 | — |
| 20[(1)] | 50 | 29 | 85 | — | 135 |
| 21 | 51 | 94 | 96 | 170 | 110 |

[(1)] full conversion of the SiH functional groups can be obtained in the presence of free 1,5-COD only if a greater concentration of [IrCODCl]$_2$ is introduced into the medium.

II. 2—Combination of Ethyl Ether and of 1,5-Cyclooctadiene (1,5-COD):

TABLE VII

| Example | Ir/ClMe$_2$SiH ($\times 10^{-6}$) | DC (%) | S (%) | Ethyl ether/Ir molar ratio | 1,5-COD/Ir molar ratio |
|---|---|---|---|---|---|
| 18 | 51 | 21 | 70 | — | — |
| 20 [(1)] | 50 | 29 | 85 | — | 135 |
| 22 | 51 | 100 | 98 | 100 | 148 |

[(1)] full conversion of the SiH functional groups can be obtained in the presence of free 1,5-COD only if a greater concentration of [IrCODCl]$_2$ is introduced into the medium.

II. 3—Combination of Benzoquinone and of 1,5-Cyclooctadiene (1,5-COD):

TABLE VIII

| Example | Ir/ClMe$_2$SiH ($\times 10^{-6}$) | DC (%) | S (%) | Benzoquinone/Ir molar ratio | 1,5-COD/Ir molar ratio |
|---|---|---|---|---|---|
| 18 | 51 | 21 | 70 | — | — |
| 20 [(1)] | 50 | 29 | 85 | — | 135 |
| 23 | 50 | 100 | 97 | 51 | 110 |

[(1)] full conversion of the SiH functional groups can be obtained in the presence of free 1,5-COD only if a greater concentration of [IrCODCl]$_2$ is introduced into the medium.

III: Example 2.4

Repetition of Example 2.1 with Regulation of the Temperature 92.48 g of allyl chloride (1.194 mol), 0.011 g of catalyst [Ir(COD)Cl]$_2$ where COD=1,5-cyclooctadiene ($2.829 \times 10^{-5}$ mol), and also COD (0.611 g, 5.648 mmol) and cyclohexanone (1.067 g, 10.9 mmol), are charged to a 500 ml four-necked glass flask equipped with a stirrer and surmounted by a reflux condenser. The mixture is stirred in order to completely dissolve the catalytic system.

The dimethylhydrochlorosilane, with a purity of 99% by weight, is introduced into the reaction medium via a peristaltic pump. 107.15 g (1.117 mol) thereof are introduced over 2 hours 30 minutes. The flow rate for introduction is adjusted in order to maintain the temperature of the reaction medium between 20 and 25° C., taking into account the high exothermicity of the reaction. The reaction medium is kept stirred for 20 minutes after the end of the introduction of the dimethylhydrochlorosilane.

At the end of this period of 20 minutes, a sample is withdrawn for analysis. The results are as follows:

DC of the dimethylhydrochlorosilane=99.8%,

S for chloropropyldimethylchlorosilane=98.3% (by analysis by gas chromatography).

The invention claimed is:

1. A method for the preparation of 3-chloropropyldimethylchlorosilane, said method comprising reacting dimethylhydrochlorosilane with allyl chloride in the presence of a catalytically effective amount of a catalyst selected from the group consisting of di-μ-chlorobis(η-1,5-hexadiene)diiridium, di-μ-bromobis(η-1,5-hexadiene)diiridium, di-μ-iodobis(η-1,5-hexadiene)diiridium, di-μ-chlorobis(η-1,5-cyclooctadiene)diiridium, di-μ-bromobis(η-1,5-cyclooctadiene) diiridium, di-μ-iodobis(η-1,5-cyclooctadiene)diiridium, di-μ-chlorobis(η-2,5-norbornadiene)diiridium, di-μ-bromobis(η-2,5-norbornadiene)diiridium, and di-μ-iodobis (η-2,5-norbornadiene)diiridium, wherein at least one auxiliary in the free or supported state formed by a mixture comprising 1,5-cyclooctadiene and a compound selected from the group consisting of cyclohexanone, ethyl ether and benzoquinone is added to the reaction mixture.

2. The method as defined by claim 1, wherein said catalyst comprises di-μ-chlorobis(η-1,5-cyclooctadiene)diiridium.

3. The method as defined by claim 1, wherein the auxiliary is introduced into the reaction medium in the free state and in a molar ratio, with respect to the iridium metal, of at least 1.

4. The method as defined by claim 1 wherein the concentration of catalyst is such that the iridium/dimethylhydrochlorosilane molar ratio is less than or equal to $100 \times 10^{-6}$.

5. The method as defined by claim 4, said molar ratio being less than or equal to $60 \times 10{-6}$.

6. The method of claim 1, wherein the degree of conversion and/or selectivity of the reaction is greater than that without adding the at least one auxiliary in the free or supported state formed by a mixture comprising 1,5-cyclooctadiene and a compound selected from the group consisting of cyclohexanone, ethyl ether and benzoquinone to the reaction mixture.

* * * * *